(12) United States Patent
Kirchner

(10) Patent No.: US 7,160,013 B2
(45) Date of Patent: Jan. 9, 2007

(54) MEDICAL DIAGNOSTIC DEVICE

(75) Inventor: Regina Kirchner, Markqröningen (DE)

(73) Assignee: Kirchner & Wilhelm GmbH & Co., KG, Asperg (DE)

( * ) Notice: Subject to any disclaimer, the term of this patent is extended or adjusted under 35 U.S.C. 154(b) by 82 days.

(21) Appl. No.: 10/977,615

(22) Filed: Oct. 27, 2004

(65) Prior Publication Data
US 2005/0107670 A1 May 19, 2005

(30) Foreign Application Priority Data
Nov. 15, 2003 (DE) ............................ 203 17 671 U

(51) Int. Cl.
*A61B 1/06* (2006.01)

(52) U.S. Cl. ................. 362/572; 362/157; 362/208

(58) Field of Classification Search ........ 600/199–200, 600/223; 362/202–206, 208, 157, 572–575
See application file for complete search history.

(56) References Cited

U.S. PATENT DOCUMENTS

| | | | | |
|---|---|---|---|---|
| 5,331,528 A * | 7/1994 | Chen | .......................... | 362/205 |
| 5,436,814 A * | 7/1995 | Hanley | ....................... | 362/216 |
| 5,733,029 A * | 3/1998 | Monroe | ....................... | 362/572 |
| 5,909,952 A * | 6/1999 | Guthrie et al. | .............. | 362/205 |
| 6,130,520 A * | 10/2000 | Wawro et al. | .............. | 320/114 |
| 6,152,873 A * | 11/2000 | Rogers | ....................... | 600/200 |
| 6,432,049 B1 * | 8/2002 | Banta et al. | ................. | 600/249 |
| 6,436,035 B1 * | 8/2002 | Toth et al. | ................... | 600/249 |
| 6,739,744 B1 * | 5/2004 | Williams et al. | ............ | 362/552 |
| 6,786,628 B1 * | 9/2004 | Steen et al. | ................. | 362/572 |
| 6,793,366 B1 * | 9/2004 | Chun | ......................... | 362/184 |
| 2004/0124782 A1 * | 7/2004 | Yu | .......................... | 315/200 A |
| 2004/0186352 A1 * | 9/2004 | Roberts et al. | ............. | 600/200 |

FOREIGN PATENT DOCUMENTS

| | | |
|---|---|---|
| DE | 202 19 984 | 4/2003 |
| GB | 2 374 402 | 10/2002 |
| WO | 02/071930 | 9/2002 |
| WO | 03/047415 | 6/2003 |
| WO | 04/084716 | 10/2004 |

* cited by examiner

*Primary Examiner*—Renee Luebke
*Assistant Examiner*—Robert May
(74) *Attorney, Agent, or Firm*—Friedrich Kueffner

(57) ABSTRACT

A medical diagnostic device with illumination, wherein the device is composed of a handle or the like in which the batteries are received and of a head which is placed on the handle. The switching transformer is arranged in a sleeve which is insertable into the handle and is electrically connected to the battery and the luminous diode.

6 Claims, 4 Drawing Sheets

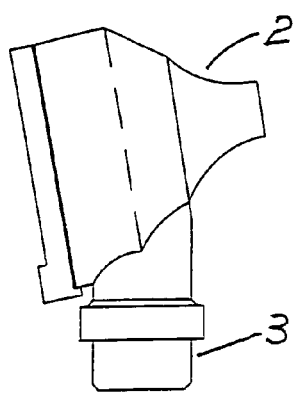
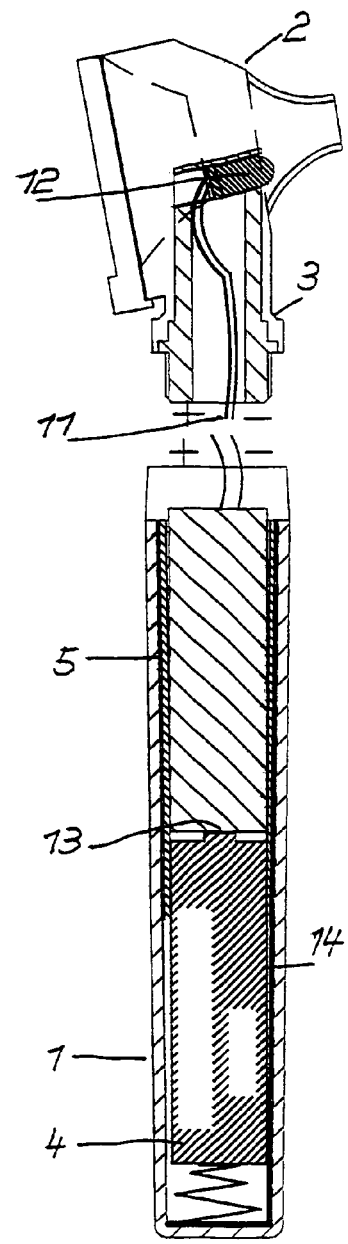
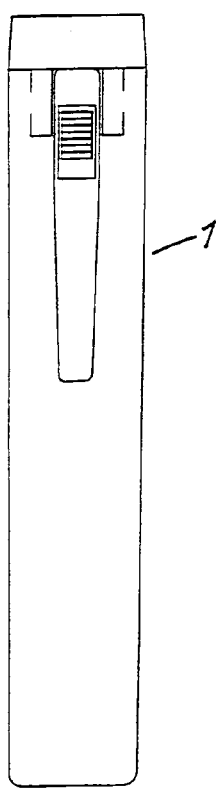

Fig. 3
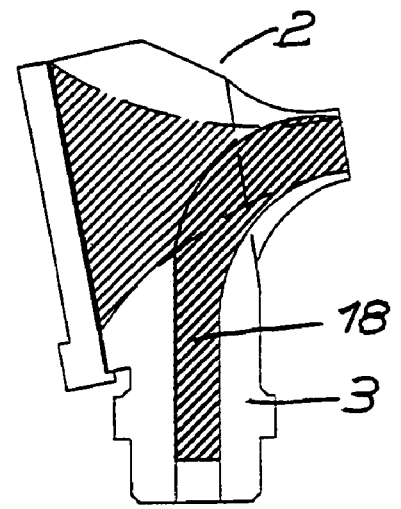
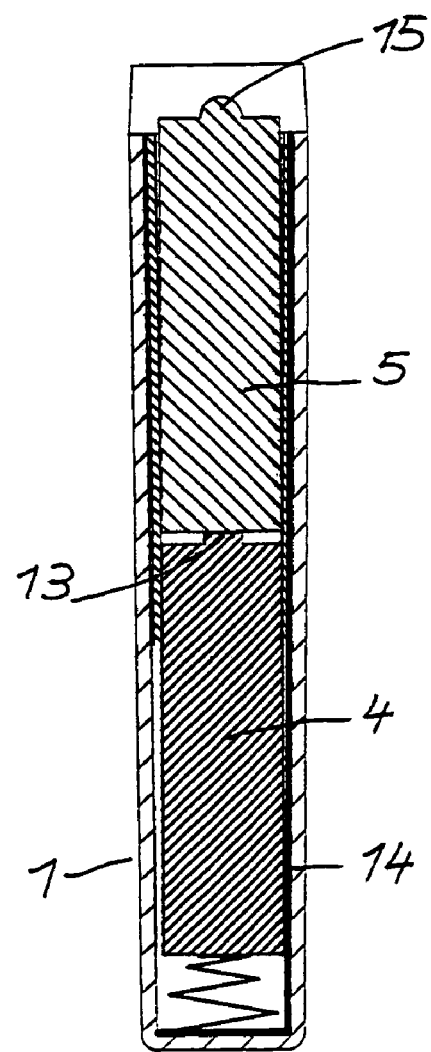

MEDICAL DIAGNOSTIC DEVICE

BACKGROUND OF THE INVENTION

1. Field of the Invention

The present invention relates to a medical diagnostic device with illumination, wherein the device is composed of a handle or the like in which the batteries are received and of a head which is placed on the handle.

2. Description of the Related Art

It is already known in the art to use luminous diodes for illumination instead of the previously used conventional incandescent lamps, because the current consumption of the incandescent lamps is relatively high and because the incandescent lamps radiate harmful heat during examinations. Luminous diodes, on the other hand, radiate heat which is hardly noticeable, take up relatively little current and have an extraordinarily long service life. However, the luminous diodes require a switching transformer in order to be supplied with current by commercially available batteries. In embodiments known in the art, the switching transformer is arranged in the head or the neck portion of the device.

SUMMARY OF THE INVENTION

It is the primary object of the present invention to provide a medical diagnostic device of the above-described type which is of simpler construction.

In accordance with the present invention, the switching transformer is arranged in a sleeve which is insertable into the handle and is electrically connected to the battery and the luminous diode.

As a result of the configuration according to the present invention, the handle can now be used for all types of diagnostic devices with various light sources and in different sizes.

The handles are usually constructed for receiving at least two batteries. Therefore, it is possible to use the same handle with two or more batteries for devices having conventional incandescent lamps as well as with a sleeve with switching transformer and a battery less for luminous diodes. Since, as already mentioned, luminous diodes consume significantly less current than an incandescent lamp, it is certainly possible to omit a battery when using luminous diodes. Another advantage of the sleeve is the fact that it can be easily replaced by the user and an incorrect mounting of the battery is practically impossible. It is of primary significance that the previously used conventional handles can still continue to be used without any alteration.

The luminous diode or the luminous diodes can be arranged in the head and can be connected through current-conducting lines to the switching transformer in the sleeve.

In accordance with another embodiment of the invention, the sleeve may have, in addition to the switching transformer, one or more luminous diodes at the end facing toward the head, wherein the light ray is then conducted through the head to one or more light conductors. It is advantageous to arrange the luminous diode or the luminous diodes in the sleeve, wherein the diode or diodes extend through one or more recesses in the sleeve.

The sleeve is advantageously connected at its lower end to one pole through a contact surface and to the other pole of the battery through a conductor extending within the battery handle.

The sleeve which is closed at the bottom is preferably composed of metal, has a plastic base in the lower portion thereof and is closed off at the top by a plastic plug. The plastic plug preferably has an opening for current conductors.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

BRIEF DESCRIPTION OF THE DRAWING

In the drawing:

FIG. 1 is an elevational view of an otoscope, wherein the head and neck are separated from the handle;

FIG. 2 is a sectional view of the otoscope of FIG. 1.

FIG. 3 is a cross-sectional view similar to FIG. 2, showing another embodiment of the otoscope;

DETAILED DESCRIPTION OF THE INVENTION

Figure 4:
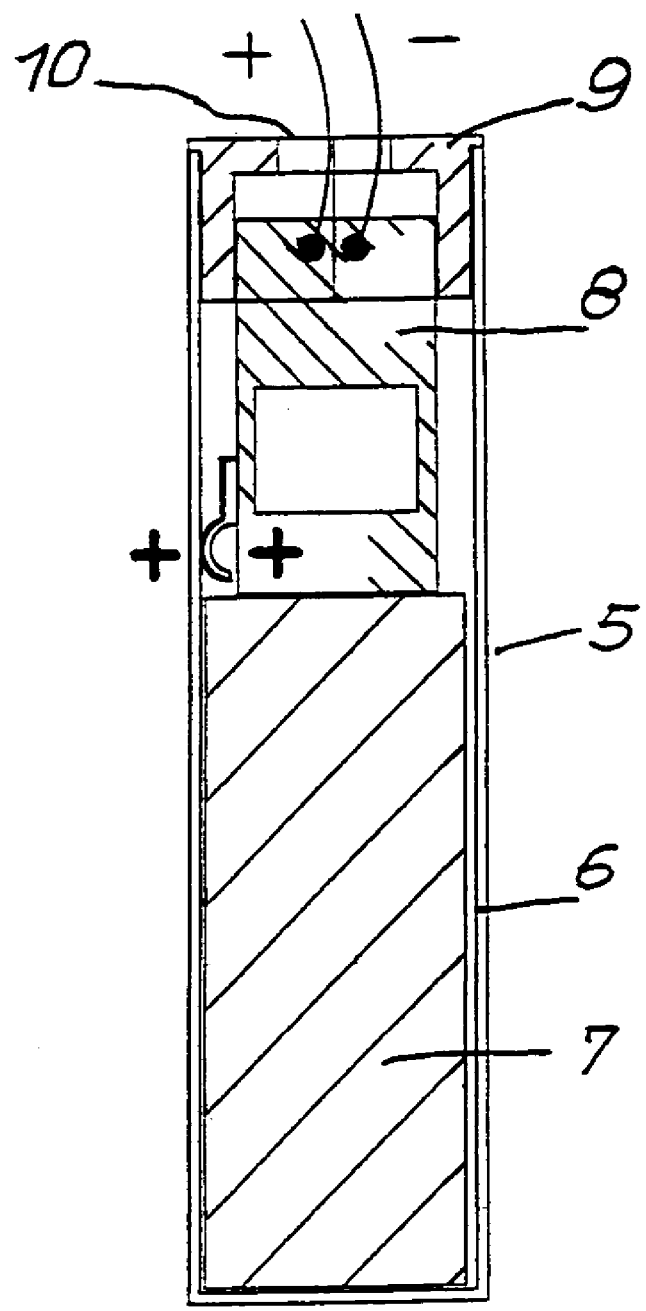
FIG. 4 is a cross-sectional view, on a larger scale, of a sleeve according to FIG. 2 with a switching transformer.

The otoscope illustrated in FIGS. 1 and 2 is composed of a handle 1 for receiving batteries and a head 2 with neck 3 which can be placed on the handle 1. In the embodiment according to FIG. 2, the handle 1 receives in the lower portion thereof a battery 4, while a sleeve 5 whose dimensions are adapted to those of a battery is arranged in the upper part instead of a second battery.

The sleeve 5 illustrated in FIG. 4 has an outer casing 6 composed of metal, wherein the lower portion of the casing 6 receives a plastic base 7. Supported on this plastic base 7 is a switching transformer 8 which adjusts the voltage supplied by the battery 4 to the voltage required for a luminous diode. In the upper part of the sleeve 5, the sleeve 5 is closed off by a plastic plug 9. The plastic plug 9 has a recess 10 for the passage of electrical conductors 11 which extend to the luminous diode 12 in the head 2, as shown in FIG. 2. The switching transformer 8 is supplied with current from the battery 4 by contacting the plus pole 13 of the battery 4 with the metal casing 6 and by contacting the minus pole through the conductor 14.

Figure 5:
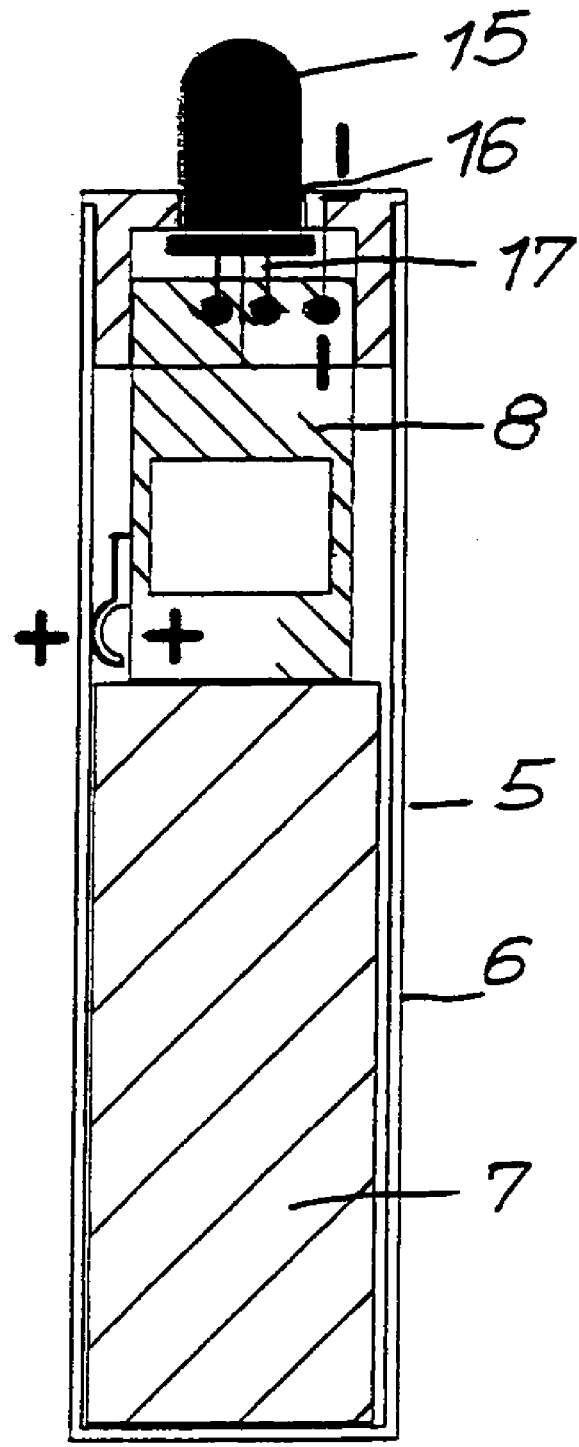
FIG. 5 is a cross-sectional view according to FIG. 4 showing another embodiment of the otoscope of FIG. 3.

In the embodiment illustrated in FIG. 3, the luminous diode 15 is not arranged in the head, but rather directly at the sleeve 5, as shown in FIG. 5. The plastic plug 9 has a larger recess 16 through which the luminous diode 15 extends, wherein the luminous diode 15 is connected at the bottom thereof through conductors 17 with the switching transformer 8. The light irradiated by this luminous diode 15 is conducted to the head 2 by light conductors 18 through the neck 3.

The invention is not limited by the embodiments described above which are presented as examples only but can be modified in various ways within the scope of protection defined by the appended patent claims.

What is claimed is:

1. A medical diagnostic device with illumination from at least one luminous diode which is supplied with current through at least one battery and a switching transformer, the device comprising a handle receiving the at least one battery and a head part placed in the handle, a sleeve insertable in the handle, wherein the switching transformer is arranged in the sleeve, and wherein electrical connections to the at least one battery and the at least one luminous diode are effected through the sleeve, wherein the sleeve has the shape of a conventional battery, and wherein the sleeve is insertable in the handle instead of an additional battery, wherein the sleeve comprises an outer casing of metal, and wherein the sleeve is closed off at a top thereof by a plastic plug, and receives at a bottom thereof a plastic base on which the switching transformer is supported.

2. The medical diagnostic device according to claim 1, wherein the sleeve has in addition to the switching transformer at least one luminous diode at an end thereof directed toward the head, and a light ray from the luminous diode is conducted through at least one light conductor to the head.

3. The medical diagnostic device according to claim 2, wherein the at least one luminous diode is arranged in the sleeve and extends through one or more recesses in the sleeve.

4. The medical diagnostic device according to claim 1, wherein the at least one luminous diode is arranged in the head and is connected through electrical conductors to the switching transformer in the sleeve.

5. The medical diagnostic device according to claim 1, wherein the sleeve is connected at the lower end thereof through a contact surface to a first pole and the sleeve is connected laterally to a second pole of the battery through a conductor extending within the handle.

6. The medical diagnostic device according to claim 1, wherein the plastic plug has an opening for the passage of current conductors.

\* \* \* \* \*